(12) United States Patent
Harry-O'Kuru et al.

(10) Patent No.: US 9,809,778 B2
(45) Date of Patent: Nov. 7, 2017

(54) POLYTRIGLYCERIDES

(71) Applicant: The United States of America, as represented by the Secretary of Agriculture, Washington, DC (US)

(72) Inventors: Rogers E. Harry-O'Kuru, Peoria, MD (US); Girma Biresaw, Peoria, IL (US); Rex E. Murray, Peoria, IL (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/134,316

(22) Filed: Apr. 20, 2016

(65) Prior Publication Data

US 2016/0312143 A1    Oct. 27, 2016

Related U.S. Application Data

(60) Provisional application No. 62/150,344, filed on Apr. 21, 2015.

(51) Int. Cl.
| | | |
|---|---|---|
| *C07C 69/716* | (2006.01) | |
| *C10M 129/95* | (2006.01) | |
| *C10M 133/54* | (2006.01) | |
| *C11C 3/00* | (2006.01) | |

(52) U.S. Cl.
CPC ......... *C10M 133/54* (2013.01); *C07C 69/716* (2013.01); *C10M 129/95* (2013.01); *C11C 3/006* (2013.01); *C10M 2207/34* (2013.01); *C10M 2215/04* (2013.01); *C10N 2230/14* (2013.01)

(58) Field of Classification Search
CPC .............. C10M 129/95; C10M 133/54; C10M 2207/34; C10M 2215/04; C10N 2230/14; C07C 69/716; C11C 3/006
See application file for complete search history.

(56) References Cited

U.S. PATENT DOCUMENTS 9,540,264 B2    1/2017   Murray et al.

FOREIGN PATENT DOCUMENTS

JP       2005133035 A  *  5/2005  ............ B82Y 30/00

OTHER PUBLICATIONS

English-language Machine translation of JP 2005-133035A.*
Lawate, S. S.; Lai., K.; Huang, C. Vegetable oils—structure and Performance. In Tribology Data Handbook; Booser, E. R., Ed.; CRC Press: New York, 1997; pp. 103-116.
ASTM D 5183-95. Standard test method for determination of the coefficient of friction of lubricants using the four-ball wear test machine. Annual Book of ASTM Standards; American Society for Testing and Materials International: West Conshohocken, PA, USA, 2002; vol. 05.03, pp. 165-169.
ASTM D 4172-94. Standard test method for wear preventive characteristics of lubricating fluid (four-ball method). Annual Book of ASTM Standards; American Society for Testing and Materials International: West Conshohocken, PA, USA, 2002; vol. 05.02, pp. 752-756.
ASTM D 2783-88. Standard test method for measurement of Extreme-pressure properties of lubricating fluids (four-ball method). Annual Book of ASTM Standards; American Society for Testing and Materials International: West Conshohocken, PA, USA, 2002; vol. 05.02, pp. 130-137.
Brown, S. F. Base oil groups; manufacture, properties and Performance. Tribol. Lubrication Technol. 2015, 71 (4), 32-35.
Harry-O'kuru, R. E., et al. Investigation of Some Characteristics of Polyhydroxy Milkweed Triglycerides and Their Acylated Derivatives in Relation to Lubircity, J. Agric. Food Chem. 2011, 59, 4725-4735.
Harry-O'Kuru, et al., Polyamine Triglycerides: Synthesis and Study of Their Potential in Lubrication, Neutralization and Sequestration, J. Agric. Food Chem. 2015, 63, 6422-6429.
Wood-Adams, P. The effect of long chain branches on the shear flow behavior of polyethylene. J. Rheol. 2001, 45, 203-210.
Shalaby, A. R. Significance of biogenic amines to food safety and human health. Food Res. Int. 1996, 29, 675-690.

* cited by examiner

*Primary Examiner* — James Goloboy
(74) *Attorney, Agent, or Firm* — John D. Fado; G. Byron Stover

(57) ABSTRACT

Disclosed herein are polyketone triglyceride compositions containing 8 to 16 ketone carbonyl moieties per triglyceride unit and methods of making. Also disclosed are polyimine triglyceride compositions having has 8 to 16 nitrogen moieties per triglyceride unit and methods of making. Also disclosed are polyamine triglyceride compositions containing 8 to 16 nitrogen moieties per triglyceride unit and methods of making.

6 Claims, 10 Drawing Sheets

Polyketone of MW Hydroxy Oil

POLYTRIGLYCERIDES

REFERENCE TO RELATED APPLICATION

This application claims the benefit of U.S. Provisional Application No. 62/150,344, filed 21 Apr. 2015, which is incorporated herein by reference in its entirety.

FIELD OF INVENTION

Disclosed are novel polyketone triglycerides, polyamine triglycerides, and polyimine triglycerides of vegetable oils. The triglyceride compositions can be used for toxic metal extraction and environmental purposes. Furthermore, the compositions can be used as biodegradable lubricating agents.

BACKGROUND OF INVENTION

The unceasing incidence of heavy and other metal pollution of the waterways and the environment is leading to increased adverse health effects on the general population, and the fines generally levied on the polluters do not resolve the persistent effects on the poisoned environment nor do these heal the people injured by such incidents. A more meaningful approach would be an effort to capture such pollutants at the source of generation. Separately, lubricating agents are base oils and additives used in lubricant formulations for engine oil, hydraulic fluids, gear oils, metal working fluids, and other applications, and consumers are seeking new and advantageous lubricating agents.

The use of vegetable oils as a source of renewable feedstock has been investigated as possible renewable feedstocks in nonfood applications (Harry-O'kuru, R. E., et. al., JAOCS, 82(3): 207-212 (2005); Harry-O'kuru, R. E., et. al., Ind. Crops and Prod., 15: 51-58 (2002);Harry-O'kuru, R. E., et al., J. Agric. Food Chem., 50: 3214-3221 (2002)). Vegetable oils typically have a triacylglycerol structure with a glycerol backbone connected to three long-chain ester linkages. The hydrocarbon chains of the structure make the molecule hydrophobic and immiscible with water or lower alcohols. The ester groups and internal double bonds give ample routes for modification (Gunstone, E., et al., Fatty Acid and Lipid Chemistry, Blackie Academic and Professional, Glasgow, UK, 1994). A wide variety of such vegetable oil derivatives having a variety of applications have been reported (Biermann et al., Angew. Chem. Int. Ed., 39: 2206-2224 (2000); Biermann et al., Angew. Chem. Int. Ed. Engl., 50: 3854-3871 (2011); Hwang et al., J. Am. Oil. Chem. Soc., 80: 811-815 (2003); Sharma et al., Bioresource Technol., 99: 7333-7340 (2008); Ionescu et al., J. Serbian Chem. Soc., 76: 591-606 (2011); Biswas et al., J. Agric. Food Chem., 56: 5611-5616 (2008); Biswas et al., Green Chem., 9: 85-89 (2007); Biswas et al., J. Agric. Food Chem., 57: 8136-8141 (2009)).

A vegetable oil of particular interest to us is a polyhydroxyl vegetable oil inasmuch as the oil has stable emulsifying properties for oil in water emulsions (Harry-O'kuru, R. E., et. al., Ind. Crops and Prod., 15: 51-58 (2002)). We believe that it would be advantageous to further modify these polyhydroxyl oils given that the feedstock material is renewable and plant based. One area of possible modification is introducing an amine function group to the oil. We synthesized α-hydroxyamine triglycerides via the oxirane triglyceride (Harry-O'kuru, R. E., et al., Ind. Crops and Prod., 15: 51-58 (2002)). Then we investigated modifications of the polyhydroxy triglyceride since it would be advantageous to further explore the functional properties of a poly (vicinal diamine) vegetable oil. Vegetable oil precursors are typically converted according to the reaction sequence:

vegetable oil triglyceride->epoxidized vegetable oil triglyceride->polyhydroxy triglyceride->polyketone triglyceride->polyimine triglyceride->polyamine triglyceride Hence, precursor of the polyhydroxy triglycerides typically involve vegetable oil epoxidation and epoxy hydrolysis reaction steps well known in the art. Typically, epoxidations are done commercially with peroxide reagents such as peracetic acid or the formic acid/hydrogen peroxide reagent. Epoxidized soybean oil is commercially manufactured (for example by Arkema and others). Hydrolysis of the epoxide can be done by acid catalyzed ring opening of the epoxide with water, thereby producing polyhydroxy triglycerides.

We have found that renewable resources in the form of vegetable oils which we have chemically modified to polyketone, polyamine, and polyimine triglyceride derivatives are capable of sequestration of toxic metal species from aqueous media. Use of these agents at the generation site of the metal species will remediate the effluents containing the toxicants and thus result in a cleaner, safer environment. The polyketone triglycerides, polyamine triglycerides, and polyimine triglycerides also are biodegradable lubricating agents.

BRIEF SUMMARY OF THE INVENTION

Disclosed herein are polyketone triglyceride compositions containing 8 to 16 (or 10-12) ketone carbonyl moieties per triglyceride unit. The polyketone triglyceride compositions may be made by methods involving providing a hydroxyl vegetable oil triglyceride having 8 to 16 (or 10-12) hydroxyl moieties per triglyceride unit, reacting the hydroxyl moieties with an oxidant, and isolating a polyketone triglyceride from the reaction of the hydroxyl vegetable oil triglyceride and oxidant.

Also disclosed are polyimine triglyceride compositions having has 8 to 16 (or 10-12) nitrogen moieties per triglyceride unit. The polyimine triglyceride compositions may be made by methods involving providing a polyketone vegetable oil triglyceride having 8 to 16 (or 10-12) ketone moieties per triglyceride unit, and reacting the ketone moieties with a primary amine moiety to form a polyimine adduct.

Also disclosed are polyamine triglyceride compositions containing 8 to 16 (10-12) nitrogen moieties per triglyceride unit. The polyamine triglyceride compositions may be made by methods involving providing a polyketone vegetable oil triglyceride having 8 to 16 (10-12) ketone moieties per triglyceride unit, reacting the ketone moieties with a primary amine moiety (as described herein) to form a polyimine adduct, and reducing the polyimine adduct to form the polyamine triglyceride.

DETAILED DESCRIPTION OF THE INVENTION

Figure 1:
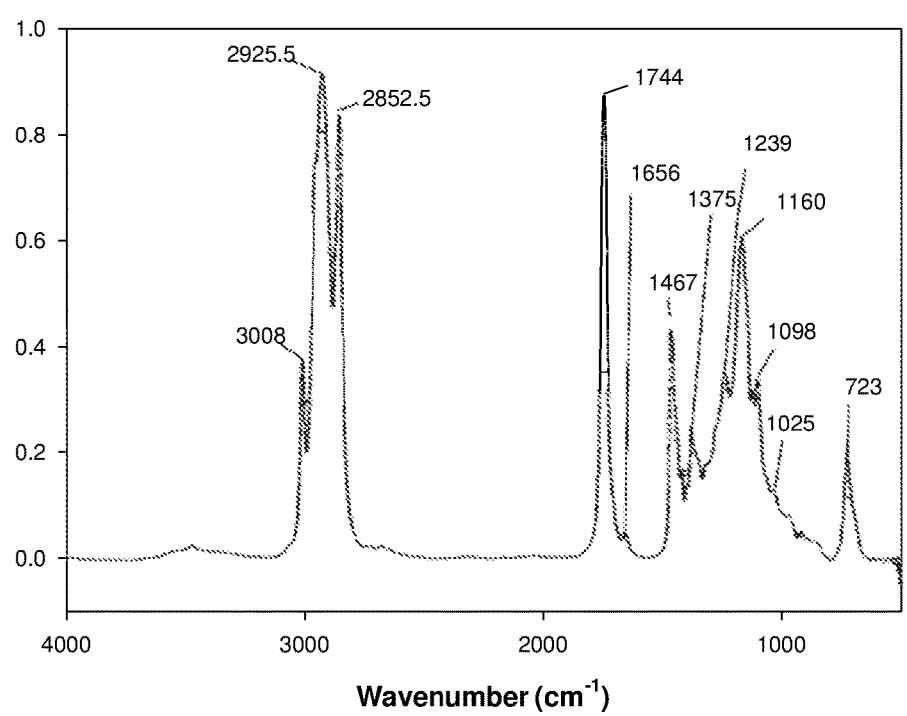
FIG. 1 depicts a FT-IR (Fourier Transform Infrared) spectrum of virgin milkweed oil as described below.

Disclosed herein are novel modified vegetable oil compositions containing oxygen and nitrogen moieties. The polyketone, polyamine and polyamine triglycerides contains 5 to 10 amine functional groups per triglyceride molecule. The amine units are located about the middle of each C18 acyl chain of the triglyceride, which introduces polarity in the middle of the naturally non-polar segment of the oil chains. This characteristic opens the oil to many useful novel behaviors including neutralization, metalworking, metal ion absorption/extraction/sequestration, etc. The impact of this polyamine could also be huge as a bio-based neutralizer. Its higher molecular mass notwithstanding, compared to current neutralization agents, it has advantages in the multiplicity of basic units in the structure. Both the polyketone and polyamine compositions will also act as an extraction/sequestration agent for metal ions (e.g., Periodic Table Elements from Group 2 to Group 14 including lanthanides and actinides like uranium recovery from sea water; for example, see metals in table 6) having high affinity for ketonate and amine ligands in the same industrial setting.

Disclosed herein are polyketone triglyceride compositions containing 8 to 16 (or 10-12) ketone carbonyl moieties per triglyceride unit. The polyketone triglyceride compositions may be made by methods involving providing a hydroxyl vegetable oil triglyceride having 8 to 16 (or 10-12) hydroxyl moieties per triglyceride unit, reacting the hydroxyl moieties with an oxidant, and isolating a polyketone triglyceride from the reaction of the hydroxyl vegetable oil triglyceride and oxidant. The method utilizes a non-aqueous solvent such as $CH_2Cl_2$, THF, EtOEt, $Ac_2O$, acetone, DCM, $H_2O$, and other known non-aqueous solvents. Since non-aqueous solvents are used, the pH of the reaction is generally not adjusted. The hydroxyl vegetable triglyceride oil may be milkweed oil, soybean oil, corn oil, linseed oil, lesquerella oil, salicornia oil, safflower oil, sunflower oil, tung oil, palm oil, palm kernel oil, castor oil, flax oil, algal oil, and mixtures thereof. Preferably the hydroxyl vegetable triglyceride oil is milkweed oil or soybean oil. The reaction is generally conducted for about 10 seconds to about 2 months (e.g., 10 seconds to 2 months; preferably about 1 minute to about 2 weeks (1 minute to 2 weeks), more preferably about 3 hours to about 1 day (3 hours to 1 day)) at a temperature of about −70° C. to about 200° C. (e.g., −70° C. to 200° C., preferably about −20° C. to about 100° C. (−20° C. to 100° C.), more preferably about −5° C. to about 25° C. (−5° C. to about 25° C.)) and at a pressure of about 0.001 atm to about 100 atm (0.001 atm to 100 atm), preferably about 0.01 atm to about 10 atm (0.01 atm to about 10 atm), more preferably about 0.1 atm to about 1 atm (0.1 atm to about 1 atm)).

The polyketone triglyceride compositions (as bio-based additives) may be used in a lubricant formulation (functional fluid) which also contains a base oil, friction modifier additive or both as an oil and additive.

Also disclosed are methods to remove metal species from a material suspected of containing one or more metal ion species, involving contacting the material with a polyketone triglyceride for a period of time and under conditions effective for sequestering the metal species by the polyketone triglyceride, and separating the polyketone triglyceride from the material. The contacting is generally for about 10 seconds to about 2 months (e.g., 10 seconds to 2 months, preferably about 10 minutes to about 2 weeks (10 minutes to 2 weeks), more preferably about 1 hour to about 72 hours (1 hour to 72 hours)) at a temperature of about −40° C. to about 200° C. (e.g., −40° C. to 200° C., preferably about −20° C. to about 80° C. (−20° C. to about 80° C.), more preferably about 5° C. to about 30° C. (5° C. to 30° C.)) at a pH of about 1 to about 13 (e.g., 1 to 13, preferably about 3 to about 11 (3 to 11), more preferably about 4 to about 9 (4 to 9)) and at a pressure of about 0.01 to about 10 atm (e.g., 0.01 atm to 10 atm, preferably about 0.1 atm to about 10 atm (0.1 to 10), more preferably about 0.1 atm to about 1 atm (0.1 atm to 1 atm). The methods may also involve recovering the polyketone triglyceride.

Also disclosed are polyimine triglyceride compositions having 8 to 16 (or 10-12) nitrogen moieties per triglyceride unit. The polyimine triglyceride compositions may be made by methods involving providing a polyketone vegetable oil triglyceride having 8 to 16 (or 10-12) ketone moieties per triglyceride unit, and reacting the ketone moieties with a primary amine moiety to form a polyimine adduct. Primary amine moieties include straight chain primary amines (e.g., aliphatic amines like methyl amine, ethyl amine, 1-propyl amine, 1-butyl amine, 1-pentyl amine, 1-hexyl amine, 1-heptyl amine, 1-octyl amine, 1-nonyl amine, 1-decyl amine, 1-dodecyl amine), branched and cyclic aliphatic amine (e.g., 2-propyl amine, 2-butyl amine, 2-pentyl amine, 3-pentyl amine, 2-hexylamine, 3-hexyl amine, 4-hexylamine, cyclohexyl amine), aromatic amines (e.g., aniline, aniline sulfate, o-anisidine, p-anisidine, anthranilic acid), functionalized amines (primary amines with functional groups, X, at the end of the chain $NH_2(CH_2)_aX$, somewhere in the chain $NH_2(CH_2)_bX$ $(CH_2)_cX$, on a branch of the chain $NH_2(CH_2)_dCH(RX)(CH_2)_eCH_3$, various combination of the above 3; examples of X include any one or various combinations of the following: —O—, —S—, —S$_x$—, —CO$_2$—, —CO$_2$H, —CON (amide), —OH, —F, —Cl, —Br, —I, —NH$_2$, —NHR, —NRR', —NH—, NR—). The methods utilize a non-aqueous solvent, and thus pH not adjusted. Preferably the polyketone triglyceride is a polyketone milkweed oil or polyketone soybean oil. The reaction is generally conducted for about 2 minutes to about 48 hours (e.g., 2 minutes to 48 hours, preferably about 5 minutes to about 24 hours (5 minutes to 24 hours), more preferably about 1 hour to about 2 hours (1 to 2 hours)) at a temperature of about −70° C. to about 200° C. (e.g., −70° C. to 200° C., preferably about −20° C. to about 100° C. −20° C. to about 100° C.), more preferably about −2° C. to about 10° C. (−2° C. to 10° C.)) and a pressure of about 0.001 atm to about 100 atm (e.g., 0.001 to 100 atm, preferably about 0.01 atm to about 10 atm (0.01 to 10 atm), more preferably about 0.1 atm to about 1 atm (0.1 atm to 1 atm)).

The polyimine triglyceride compositions (as bio-based additives) may be used in a lubricant formulation (functional fluid) which also contains a base oil, friction modifier additive or both as an oil and additive.

Also disclosed are methods to remove metal species from a material suspected of containing one or more metal ion species, involving contacting the material with a polyimine triglyceride thereof for a period of time and under conditions effective for sequestering the metal species by the polyimine triglyceride, and separating the polyimine triglyceride from the material. Generally the contacting is for about 10 seconds to about 2 months (e.g., 10 seconds to 2 months, preferably about 10 minutes to about 2 weeks (10 minutes to 2 weeks), more preferably about 1 hour to about 72 hours (1 hour to 72 hours)) at a temperature of about −40° C. to about 200° C. (e.g., −40° C. to 200° C., preferably about −20° C. to about 80° C. (−20° C. to about 80° C.), more preferably about 5° C. to about 30° C. (5° C. to about 30° C.)) at a pH of about 1 to about 13 (e.g., 1 to 13, preferably about 3 to about 11 (3 to 11), more preferably about 4 to about 9 (4 to 9)) and at a pressure of about 0.001 atm to about 100 atm (e.g., 0.001 atm to 100 atm, preferably about 0.01 atm to about 10 atm (0.01 atm to 10 atm), more preferably about 0.1 atm to about 10 atm (0.1 atm to 10 atm)). The method may further involve recovering the polyimine triglyceride.

Also disclosed are polyamine triglyceride compositions containing 8 to 16 (10-12) nitrogen moieties per triglyceride unit. The polyamine triglyceride compositions may be made by a method involving providing a polyketone vegetable oil triglyceride having 8 to 16 (10-12) ketone moieties per triglyceride unit, reacting the ketone moieties with a primary amine moiety (as described herein) to form a polyimine adduct, and reducing the polyimine adduct to form the polyamine triglyceride. The method is generally conducted for about 2 minutes to about 48 hours (e.g., 2 minutes to 48 hours), preferably about 5 minutes to about 24 hours (5 minutes to 24 hours), more preferably about 1 hour to about 8 hours (1 hour to 8 hours)) at a temperature of about −40° C. to about 150° C. (e.g., −40° C. to 150° C., preferably about −20° C. to about 100° C. (−20° C. to about 100° C.), more preferably about 0° C. to about 25° C. (0° C. to about 25° C.)) and at a pressure of about 0.001 atm to about 100 atm (e.g., 0.001 atm to 100 atm, preferably about 0.01 atm to about 10 atm (0.01 atm to 10 atm), more preferably about 0.1 atm to about 1 atm (0.1 atm to 1 atm)). Reducing the polyimine adduct may utilize borohydride or hydrogen or other mild selective reducing agents for imines in the presence of esters, cyanoborohydride (An aryloxotitanium complex is a highly chemo- and regioselective catalyst for intermolecular hydroamination of terminal alkynes. Branched imines are obtained in good yields with various primary aromatic and aliphatic amines, Khedka, V., A. Tillak, M. Bella, Org. Lett., 5: 4767-4770 (2003)); DiethylZinc/Ni(acacac)$_2$ in presence of ketones (Xue Xio, Haowei Wang, Zhiyng Huang, Jun Yang, Xiaoxia Bian and Yong Quin, Selective Diethylzinc reduction of imines in the presence of ketones, Organic Letters, 8(1): 139-142 (2006); HCl$_3$/CH$_3$CN/80° C. (Mild and selective reduction of imines: Formation of an unsymmetrical macrocycle, Amanda, J., Gallant, Brian O. Patrick, and Mark J. MacLachlan, J. Org. Chem., 69, 8739-8744 (2004); Reductive amination of ketones and aldehydes with RaNi, H$_2$, NH$_3$ (V. A. Tarasevich and N. G. Kozloz, Reductive amination of oxygen-containing organic compounds, Russian Chem. Reviews, 68(1): 55-72 (1999); Colin J. Dunsmore, Reuben Can, Toni Fleming, and Nicholas J. Turner, A. Chemo-enzymatic route to enantiomerically pure cyclic tertiary amines, J. Am. Chem. Soc., 128(7): 2224-2225 (2006)).

The polyamine triglyceride compositions (as bio-based additives) may be used in a lubricant formulation (functional fluid) which also contains a base oil, friction modifier additive or both as an oil and additive.

Also disclosed are methods to remove metal species from a material suspected of containing one or more metal ion species, involving contacting the material with a polyamine triglyceride thereof for a period of time and under conditions effective for sequestering the metal species by the polyamine triglyceride thereof, and separating the polyamine triglyceride from the material. The contacting is generally for about 10 seconds to about 2 months (e.g., 10 seconds to 2 months, preferably about 10 minutes to about 2 weeks (10 minutes to 2 weeks), more preferably about 1 hour to about 72 hours (1 hour to 72 hours)) at a temperature of about −40° C. to about 200° C. (e.g., −40° C. to 200° C., preferably about −20° C. to about 80° C. (−20° C. to about 80° C.), more preferably about 5° C. to about 30° C. (5° C. to about 30° C.)) at a pH of about 1 to about 13 (e.g., 1 to 13, preferably about 3 to about 11 (3 to 11), more preferably about 4 to about 9 (4 to 9)) and at a pressure of about 1 torr to 1000 psi (e.g., 1 torr to 1000 psi, preferably about 10 torr to 10 atm (10 torr to 10 atm, more preferably about 100 torr to 1 atm (100 torr to 1 atm). The method may further involve recovering the polyamine triglyceride.

One component of the reaction mixtures described herein is a vegetable oil. Examples of suitable vegetable oils include but are not limited to soybean oil, safflower oil, linseed oil, corn oil, sunflower oil, olive oil, canola oil, sesame oil, cottonseed oil, palm oil, rapeseed oil, tung oil, peanut oil, cuphea oil, milkweed oil, physaria oil, salicornia oil, and combinations thereof. Natural vegetable oils may be used, and also useful are partially hydrogenated vegetable oils and genetically modified vegetable oils, including safflower oil, high oleic soybean oil, high oleic peanut oil, high oleic sunflower oil, and high erucic rapeseed oil (crambe oil). The term "vegetable oil" herein includes all of the above examples. The term "vegetable oil" also includes high oleic oils containing high levels of triolein which would give only 6 ketone carbonyls in a triglyceride as the major component, but given one linoleate with two oleates in the oil it would give 8 ketone carbonyls as a minor component.

In a preferred embodiment wherein the fatty acids are present as triglycerides, the oils principally contemplated herein include what are normally referred to as the triglyceride drying oils. Because of ready availability and low cost, the preferred vegetable oil used herein is soybean oil or milkweed oil. The fatty acid constituents of soybean oil are mainly oleic (18:1), linoleic (18:2), and linolenic (18:3) acids. Though the relative distribution of fatty acids is largely dependent on the seed type and its genetic makeup, soybean oil typically consists of approximately $C_{16:0}$=4%, $C_{18:0}$=3%, $C_{18:1}$=22%, $C_{18:2}$=66%, and $C_{18:3}$=5%.

The practitioner skilled in the art will of course recognize that for fatty acid products requiring a high degree of purity or uniformity, the oils may first be hydrolyzed to obtain free fatty acids for use as starting materials in the reaction. Hydrolysis of the oils to the fatty acids may be achieved using conventional splitting techniques or alkali splitting of fats. Suitable alkali splitting techniques include, treatment with sodium methoxide or sodium or potassium hydroxide (see "A.O.C.S. Tentative Method Ca 6b-53" IN Official and Tentative Methods of the American Oil Chemist's Society, third edition, AOCS, Chicago, Ill. (1973)). Other conventional techniques, including splitting with steam under pressure, are also effective.

The nitrogen or amine fatty acid derivatives of this invention have properties which render them useful as additives to base stocks for biodegradable lubricant applications, such as crankcase oils, transmission fluids, two-cycle engine oils, marine engine oils, greases, hydraulic fluids, drilling fluids, metal cutting oils, and the like. Base stocks useful in the lubricant formulations contemplated by the invention are typically high molecular weight hydrocarbons, and may be of mineral, vegetable, or synthetic origin, or mixtures thereof. Exemplary base oils are described in Erickson et al. (U.S. Pat. No. 5,023,312).

Formulations of base stocks with the polyketone triglycerides, polyamine triglycerides, and polyimine triglycerides of the invention may meet or exceed many, if not all, specifications for lubricant end-use applications. It is contemplated that other additives may be used in conjunction with the nitrogen or amine fatty acid derivatives in order to enhance the properties of the base stock. Illustrative of such additives are detergents, anti-wear agents, antioxidants, viscosity index adjusters, pour point depressants, corrosion protectors, friction coefficient modifiers, colorants, and the like as well-known in the art. Other additives may be added to the composition disclosed herein provided they do not substantially interfere with the intended activity and efficacy of the composition; whether or not a compound interferes with activity and/or efficacy can be determined, for example, by the procedures utilized below.

In accordance with the processes disclosed herein, the material suspected of containing or being contaminated with metals (e.g., Periodic Table Elements from Group 2 to Group 14 including lanthanides and actinides) is contacted with the polyketone triglycerides, polyamine triglycerides, or polyimine triglycerides for a period of time and under conditions effective for the metal species in the material to be sequestered by the triglycerides. The specific contact time will vary with the material being treated and particularly its phase (solid, liquid or gas), the type of contactor used as discussed below, and the metal species concentration in the treated material and the desired final concentration therein (i.e., complete vs. partial removal), and may be readily determined empirically by the skilled user. After this contact, the resultant composition having the metals sequestered therein may be separated from the treated material. The remaining treated material, having its metal content significantly reduced or eliminated, may be subsequently recovered. The process may be conducted as a batch, semi-batch, or continuous system. In an optional embodiment, the recovered treated materials, and particularly those processed in batch or semi-batch systems, may be contacted one or more times with fresh polyketone triglycerides, polyamine triglyceride, or polyimine triglycerides to further decrease the metal species concentration therein to the desired level.

Disclosed herein are novel modified vegetable oil compositions containing oxygen and nitrogen moieties. The compositions contain polyamine triglyceride containing 8 to 16 amine functional groups per triglyceride molecule. The amine units are located about the middle of each acyl chain (e.g., C18) of the triglyceride, which introduces polarity in the middle of the naturally non-polar segment of the oil chains. This characteristic opens the oil to many useful novel behaviors including neutralization, metalworking, metal ion absorption/extraction/sequestration, etc. Also, the novel polyketone triglyceride precursor, in its own right, has applications for metal absorption/sequestration. The polyamine can be used as a bio-based neutralizer. Its higher molecular mass notwithstanding, compared to current neutralization agents, it has advantages in the multiplicity of basic units in the structure. Both the polyketone and polyamine compositions will also act as an extraction/sequestration agent for metal ions having high affinity for ketonate and amine ligands in the same industrial setting.

Suitable oxidants can be selected from three general classifications: Class 1 is non-metal oxidants, Dess-Martin Periodinane reagent, also acetic anhydride-dimethylsulfoxide oxidation (see, for example, Kiely, D. E., and H. G., Fletcher, Chemical synthesis of D-xylo-hexos-5-ulose 6-phosphate, a putative intermediate in biosynthesis of myo-inositol, JOC, 33: 3723-3727 (1968); Albright, J. D., and L. Goldman, Dimethyl sulfoxide-acid anhydride mixtures. New reagents for oxidation of alcohols, J. Amer. Chem. Soc., 87(18): 4214-4216 (1965)); Class 2 is metal-containing oxides such as ruthenium dioxide-potassium meta periodate (see, for example, Stevens, C. L., and C. P. Bryant, Ruthenium dioxide-potassium meta-periodate. Methods in Carbohydr. Chem., 6(59): 337-341 (1972)); Class 3 is catalysts such as hydrogen transfer catalysts such as Ru3(CO) 12-acetone (Basu, S. Bhaduri, H. Khwaja, and K. R. Sharma, Homogeneous Catalytic Hydrogenation, Transfer Hydrogenation, and Nitrobenzene Carbonylation Reactions With [Ru3(CO)12] As The Catalyst, Proc. Indian Natn. Sci. Acad., 52A, No, 4, pp. 831-836 (1986)).

As used in the specification and claims, the singular form "a", "an" and "the" include plural references unless the context clearly dictates otherwise.

"Optional" or "optionally" means that the subsequently described event or circumstance may or may not occur, and that the description includes instances in which said event or circumstance occurs and instances where it does not. For example, the phrase "optionally comprising a defoaming agent" means that the composition may or may not contain a defoaming agent and that this description includes compositions that contain and do not contain a foaming agent.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

The amounts and ranges disclosed herein are not meant to be limiting, and increments between the recited percentages and ranges are specifically envisioned as part of the invention.

Unless defined otherwise, all technical and scientific terms used herein have the same meaning as commonly understood by one of ordinary skill in the art to which the invention belongs. As used herein, the term "about" refers to a quantity, level, value or amount that varies by as much as 30%, preferably by as much as 20%, and more preferably by as much as 10% to a reference quantity, level, value or amount. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Example 1

Synthesis of Milkweed polyketone from Polyhydroxy Milkweed oil. In a typical reaction, polyhydroxy milkweed oil (61.0 g, 57.72 mmol) previously derived from milkweed oil (Harry-O'kuru, R. E., et al., Ind. Crops and Prod., 15: 51-58 (2002)) was placed into a 500 mL dry round-bottomed flask (RBF) containing a magnetic stir bar. Dry dichloromethane (150 mL) was then added and stirred to dissolve the oil. The stirred solution was cooled to −5° C. in an ice bath augmented with NaCl. Dess-Martin Periodinane reagent (59.5 g, 140 mmol) was added quickly while stirring was continued. The reaction temperature was gradually allowed to warm to 0° C. over 3 h then to room temperature overnight. A yellow solid formed which later was redissolved in the dichloromethane. The resulting mixture was then concentrated to dryness under reduced pressure and the solid was triturated with anhydrous EtOEt (100 mL×3) and filtered. The filtrate was washed with saturated $NaHCO_3$. The organic layer was rewashed with a mixture of $NaHCO_3$—$Na_2S_2O_3.5H_2O$ (120 mL). After separation of phases, the organic layer was rewashed with brine and dried over $MgSO_4$ overnight. The filtrate was then concentrated under reduced pressure to give 60.7 g (99.0%) yield of the polyketone triglyceride. The FT-IR spectrum of the product obtained was $v_{NCl}$ $cm^{-1}$: 2927 vs (—$CH_2$— asym stretch), 2858 s (—$CH_2$— sym stretch), 1744 vs ($2^{nd}$ derivative C═O) ester; 1720 s-m (ketone C═O), 1463 m (—$CH_2$— deform), 1370 m (—$CH_3$ deform), 1235 m (C—OC—) stretch, 1166 s (—HC—O) stretch, 1097 m (—HCO—) stretch, 1020 m (—$CH_2$O—) stretch, 723 w (—$CH_2$—)wag; $^{13}C$ NMR ($CDCl_3$) δ: 213.6, 213.27, 209.7, 208.5, 206.6, 205.58, 205.52, 202.93, 202.8 (polyketone C═O).

Milkweed Schiff Base Formation from the Polyketone: Milkweed polyketone triglyceride (161.3 g, 156.5 mmol) was placed in a dry 1L round-bottomed flask containing a magnetic stirrer. Dry dichloromethane (300 mL) was added and the mixture stirred and cooled to −1° C. in an ice bath; 2-propylamine (92.45 g, 1.564 mol) was then added dropwise to maintain the reaction temperature at 0° C. After all the amine had been added, the temperature was slowly allowed to warm to room temperature overnight. The solvent was removed under reduced pressure at 50° C. and the crude product was diluted with EtOAc and dried over $MgSO_4$, filtered and concentrated under reduced pressure followed by pump vacuum drying to give a yield of 158.8 g (70.6%) of the Schiff base. FT-IR spectrum $cm^{-1}$: 3366 w, 2928 vs, 2855 s, 1740s (—C═O), 1659, 1565 (—C═N— of Schiff base), 1462 (—$CH_2$ -deform), 1375 (—$CH_3$ deform), 1244, 1164, 1090, 726; $^{13}CNMR$ ($CDCl_3$) δ: 173.19, 172.77, 172.46, 171.15, (C═O ester), 160.69 (C═O formyl ester), 68.88 (—CH-glyceride β-carbon), 63.75 methine carbon of isopropyl), 62.06, 60.36(—$CH_2$O-glyceride α- and γ-backbone), 44.44, 43.72, 41.19, 40.30, 38.58 (—CH-isopropyl), 34.07-21.71 (—$CH_2$—), 20.98-13.89 (—$CH_3$).

Conversion of the Schiff base (Imine) Triglyceride to the Polyamine Triglyceride: The intermediate imine triglyceride (155.7 g, 0.1084 mmol) dissolved in a 50/50 EtOH (300 mL), 1,4-Dioxane (300 mL) was placed in a 1L round-bottomed flask containing a magnetic stir bar. Acetic acid (3 mL) was added to the solution and the mixture vigorously stirred and cooled to 0° C. in an ice bath. Powdered $NaBH_4$ (40.0 g) was added portion-wise to maintain the reaction temperature around 0° C. At the end of the borohydride addition, the reaction was allowed to stir overnight warming to RT. The mixture was then diluted to 1000 mL with 3% aqueous acetic acid (AcOH) solution followed by extraction with dichloromethane. The extract was then washed with distilled water, dried over $MgSO_4$ and concentrated under reduced pressure at 48° C. followed by further drying at the pump to yield the polyamine product (160.2g). Density at 24° C. was 1.072 $g.cm^{-3}$; pH 8.09 (EtOH). FT-IR (NaCl film) v $cm^{-1}$: 3382 (—N—H stretch), 2962 (—$CH_3$ asym), 2929 (—$CH_2$— asym) vs, 2873 (—$CH_3$ sym), 2856 s (—$CH_2$— sym), 1741 vs (C═O ester backbone), 1664 m, 1549 m-w (N—C), 1470 s (—$CH_2$— def.), 1376 s (—$CH_3$ def.), 1256, 1240 s (—C—O—C═O), 1167 s, 1109 s, 875, 722 (—$CH_2$—) wag; $^{13}C$-NMR DEPT ($CDCl_3$) δ: 176.67 (C═O ester), 160.96 (—HC═O), 82.45, 81.54, 80.90, 80.11, 73.81, 71.85, 68.88, 67.02, 65.80 (—CHN—), 62.05, 60.14 (—$CH_2$O—), 57.25, 43.55, 41.19, 40.28, 35.94-22.63 (—$CH_2$—), 21.08-14.19 (—$CH_3$).

Figure 2:
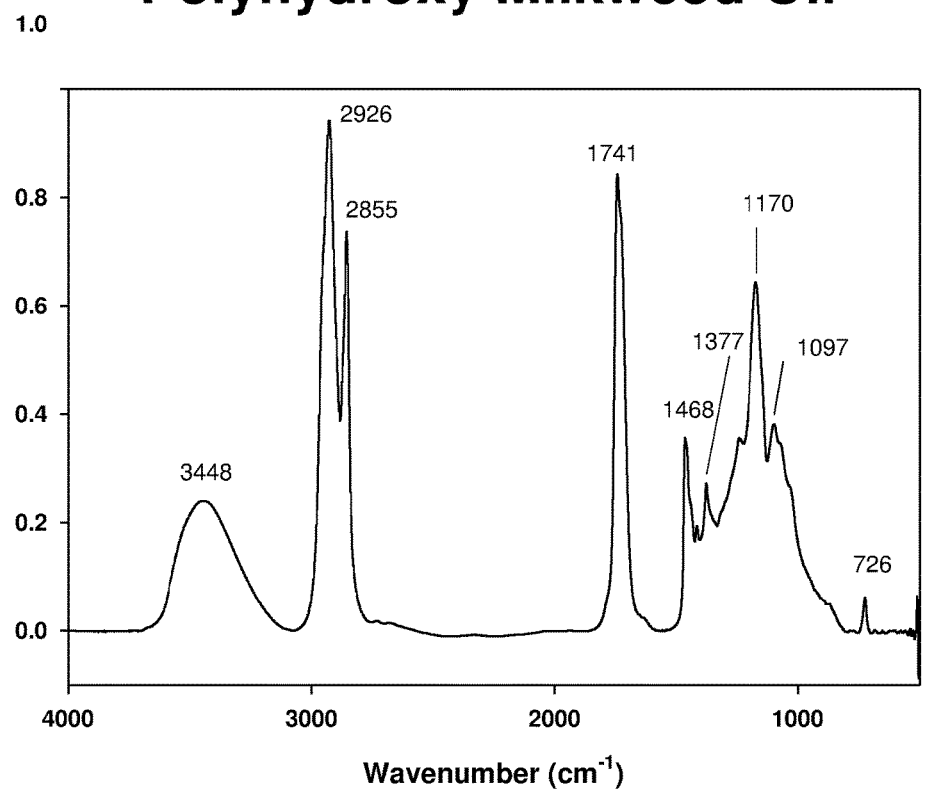
FIG. 2 depicts a FT-IR spectrum of milkweed polyhydroxy triglyceride generated from hydration of epoxide moieties of virgin milkweed oil as described below.
Figure 3:
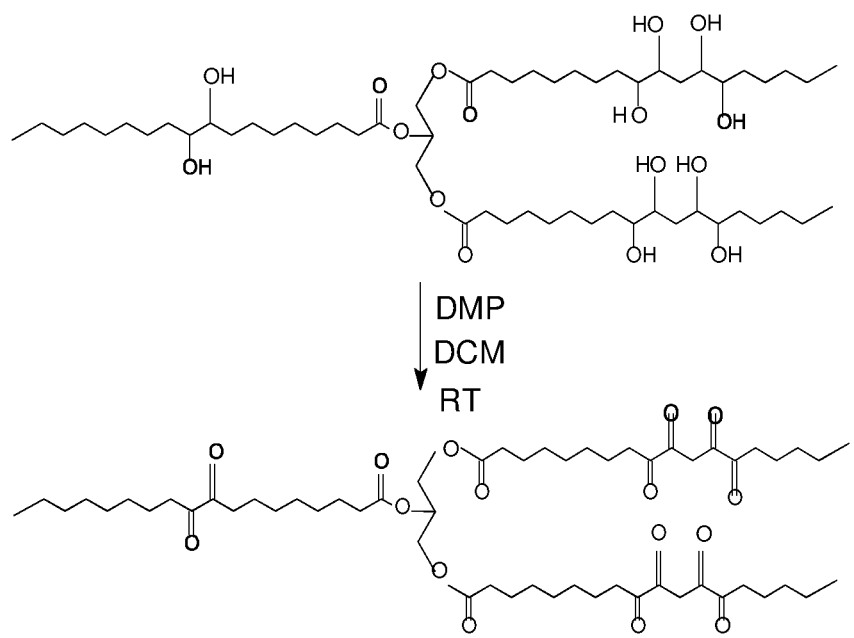
FIG. 3 depicts a schematic for the oxidation of milkweed polyhydroxy oil to the polyketone via an oxidant (e.g., Dess-Martin Periodinane (DMP)) as described below.
Figure 4:
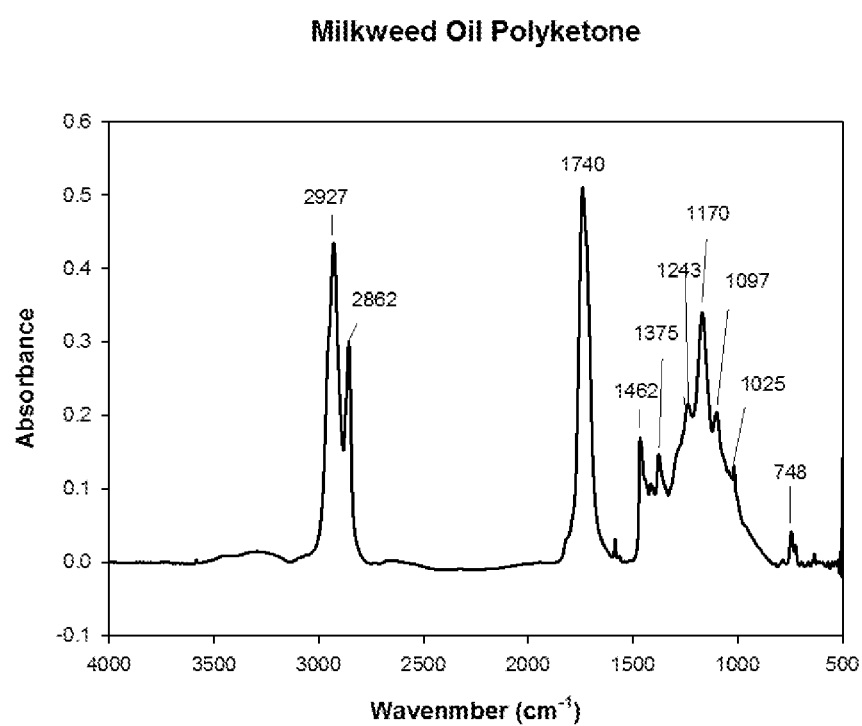
FIG. 4 depicts a FT-IR spectrum of milkweed polyketone triglyceride as described below.
Figure 5:
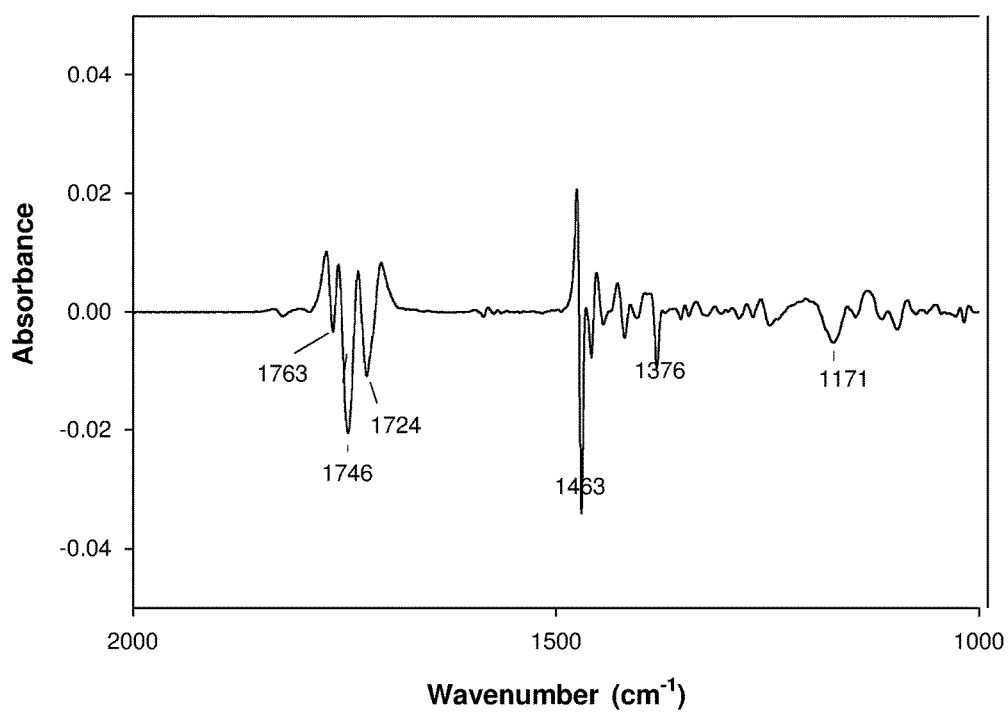
FIG. 5 depicts a FT-IR carbonyl spectral region of $2^{nd}$ derivative at 1763-1724 cm$^{-1}$ showing keto carbonyl at 1724 and ester carbonyl absorption at 1746 cm$^{-1}$, respectively, as described below.
Figure 6:
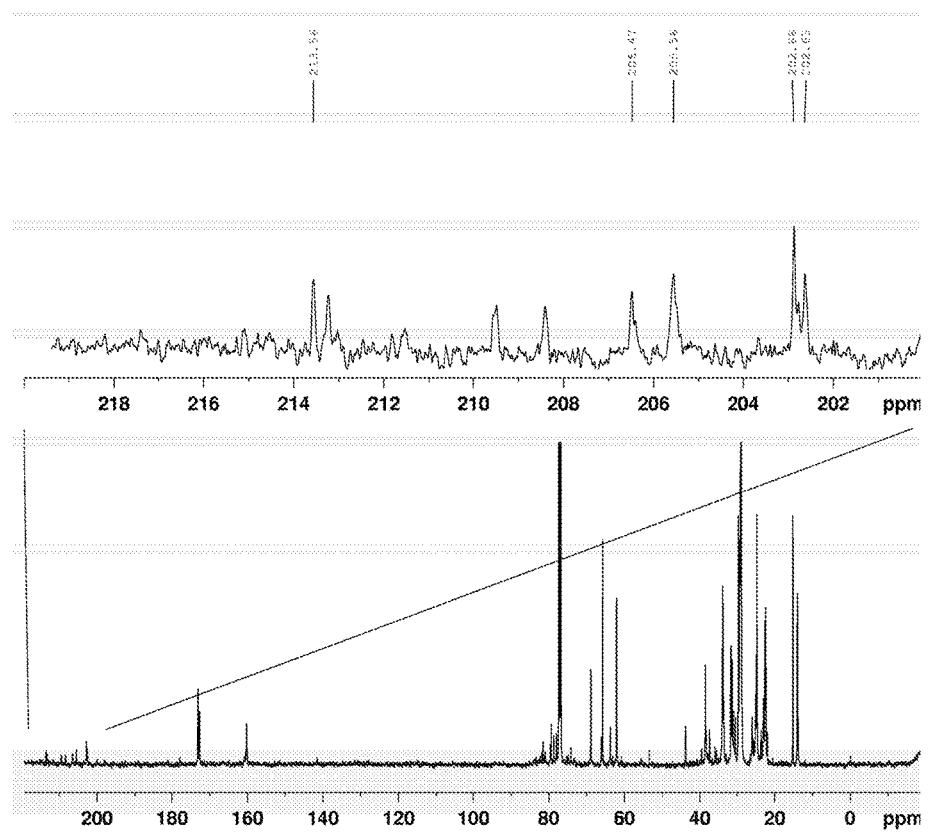
FIG. 6 depicts a $^{13}$C-NMR spectrum of milkweed oil polyketone showing keto carbonyl resonances as described below.

Synthesis and identification of Milkweed Polyamine: The FT-IR spectrum of the unmodified milkweed oil is shown in FIG. 1. This spectrum displayed the olefinic —C═C—H absorption mode at around 3009 $cm^{-1}$ as well as the breathing or puckering mode of the C═C bond at around 1658 $cm^{-1}$. In contrast, the starting polyhydroxy oil, FIG. 2, exhibited the characteristic broad (O—H) stretching band centered at 3448 $cm^{-1}$. This spectral region was transparent in the virgin oil. Substitution of the hydroxyl groups of polyhydroxy milkweed oil with nitrogen proceeded through an intermediate polyketone triglyceride of milkweed oil shown in FIG. 4. An initial attempt at oxidation of the polyhydroxy oil (FIG. 2) to the polyketone using the Jones reagent (chromic acid/$H_2SO_4$) resulted in an isolated product which was characteristically not the desired material judging from the $^{13}C$-NMR spectrum obtained (not shown here). However, use of the Dess-Martin Periodinane reagent cleanly oxidized the polyhydroxy oil to give an excellent, almost quantitative yield of the polyketone triglyceride. FIG. 3 shows the synthetic procedure used; spectroscopic characterization of the polyketone is shown in FIGS. 4-6. FIG. 4 and FIG. 5 are the FT-IR spectra of the polyketone the $2^{nd}$ derivative of which depicts the carbonyl region of the spectrum with three bands indicating the keto absorbance at 1724 $cm^{-1}$, the carbonyl absorption of the polar head groups triglyceride at 1746 $cm^{-1}$ and a smaller higher frequency band at 1763 $cm^{-1}$. The $^{13}C$-NMR spectrum of a very dry sample of this intermediate (FIG. 6) clearly showed the polyketo resonances (10 lines) from 202.8-213.6 ppm corresponding to some 10 keto carbonyl groups expected in this intermediate from the 10 secondary hydroxyl groups of the polyhydroxy starting material.

The arrangement of these carbonyl groups in this intermediate was such that on its own it would surprisingly form a number of coordination complexes with metal ions. It is contemplated that such an arrangement would be useful in removing metal ions in environmental remediation purposes, particularly oxophilic metal ions such as Group 2 (IIA) elements. This is borne out when the material is not intensely dry and enolization becomes plainly evident in the $^{13}C$-NMR exhibiting typical enolic carbon resonances around 96 ppm and 191 ppm as well as resonances of the unenolized carbonyls for the intact keto forms between 205 and 214 ppm. The segments of the structure that behaved this way were the two carbonyls at C10 and C12 separated by the C11 methylene protons which became acidic by virtue of being sandwiched between the two carbonyls. This segment of the oil bears a strong resemblance to the molecular structure of 2,4-pentanedione (acetyl acetone) which tends to be predominantly in the enolic tautomeric form and is a known strong metal chelating agent. Thus under appropriate conditions this polyketone intermediate is expected to show powerful chelating properties.

Figure 7:
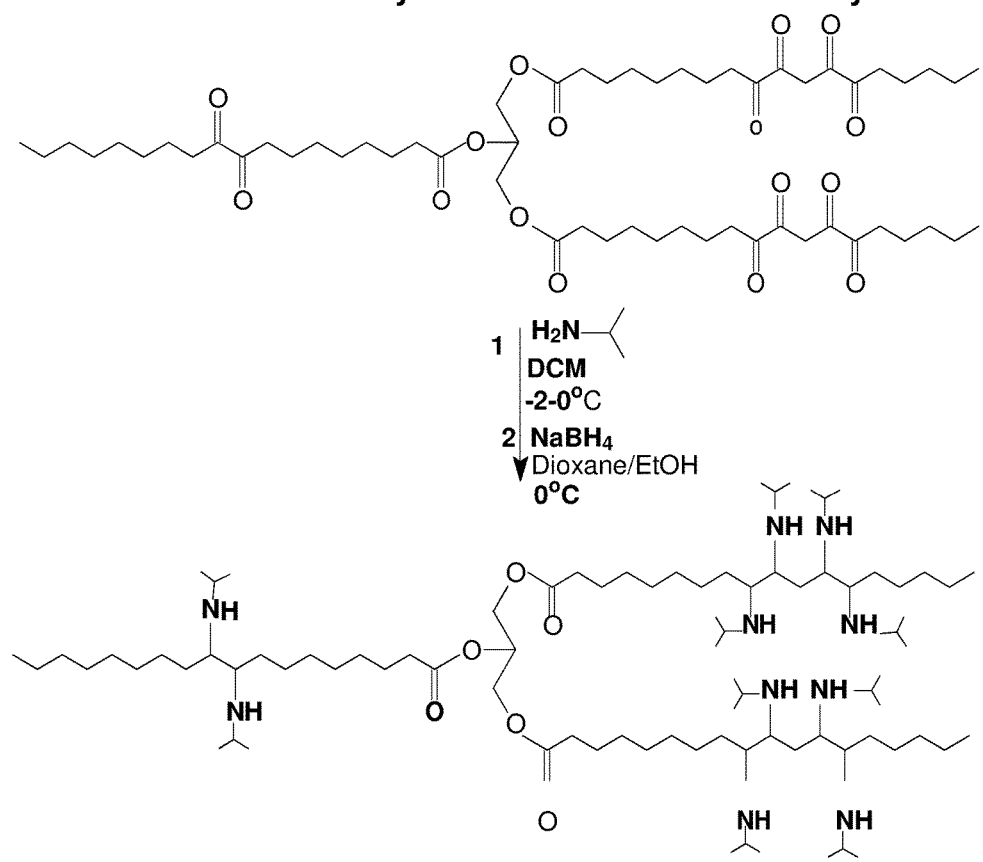
FIG. 7 depicts a schematic for Schiff base formation from milkweed oil polyketone reaction with 2-propylamine followed by sodium borohydride reduction to the polyamine triglyceride as described below.
Figure 8:
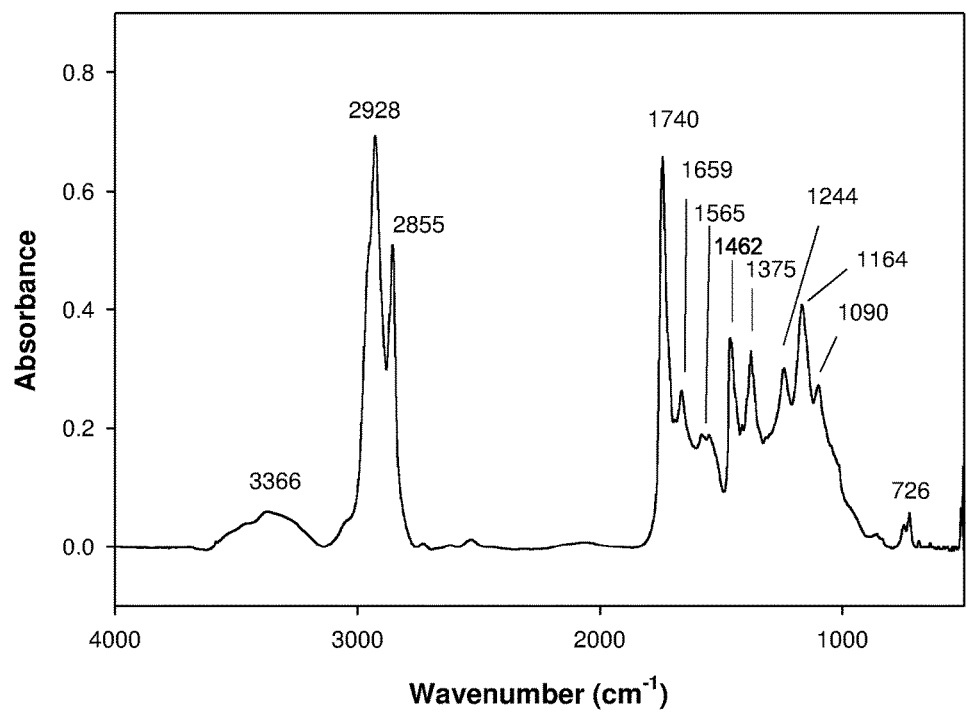
FIG. 8 depicts a FT-IR spectrum of the polyimine (Schiff Base) as described below.
Figure 9:
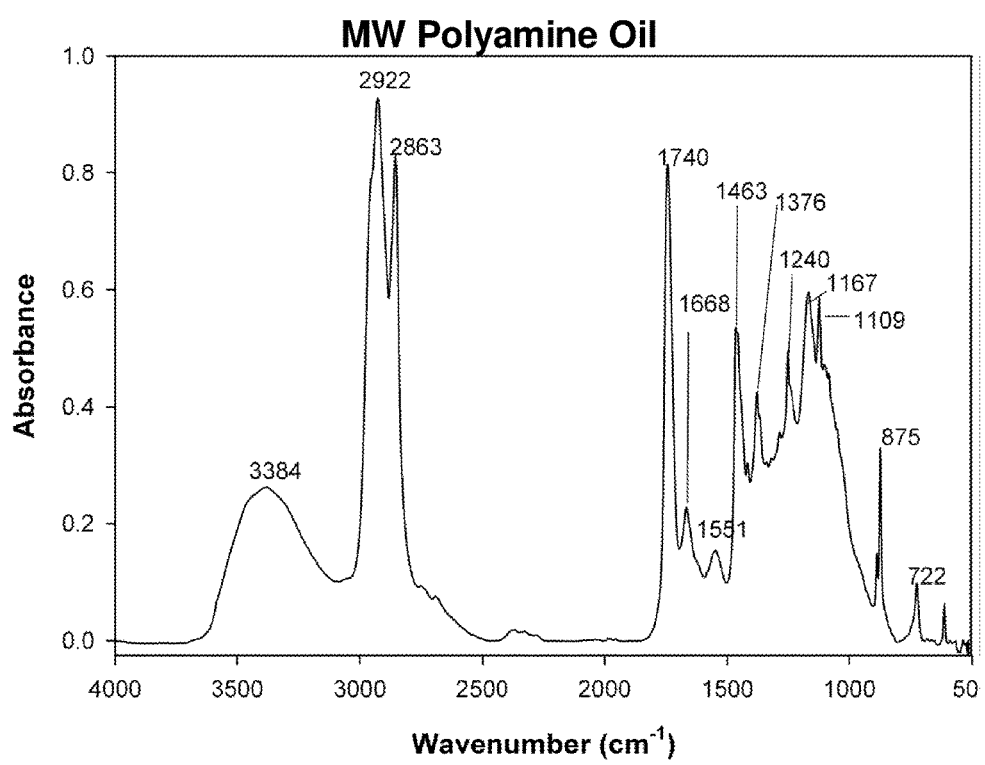
FIG. 9 depicts a FT-IR spectrum of milkweed polyamine following reduction of Schiff base as described below.
Figure 10:
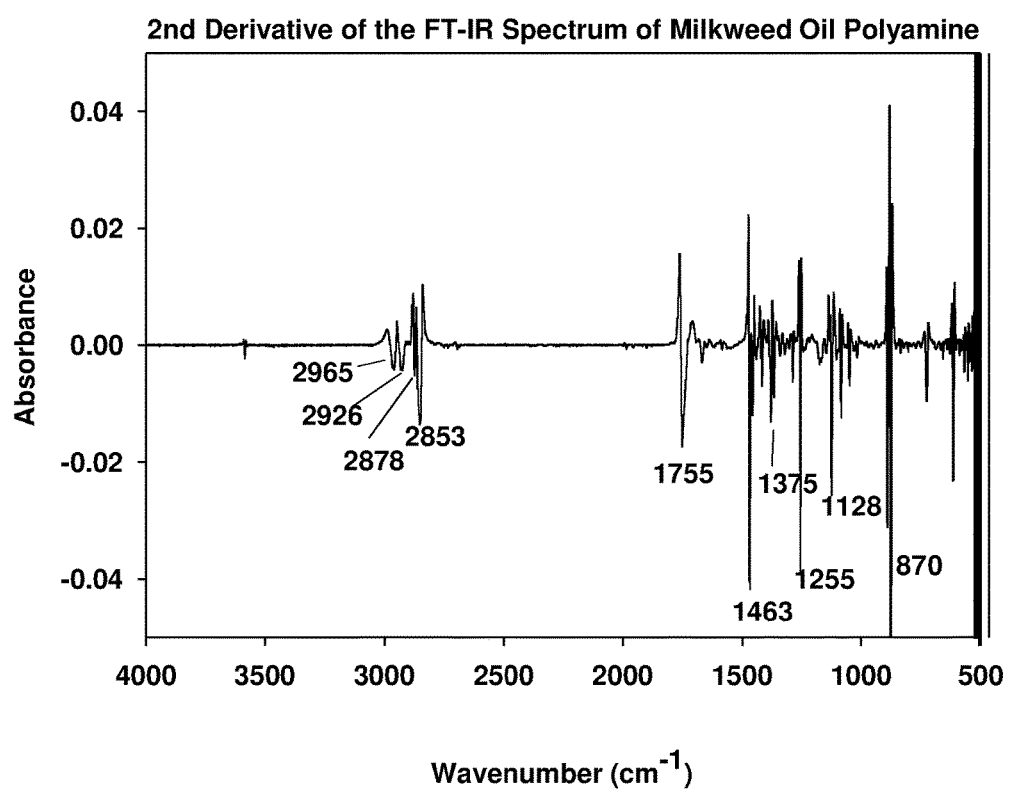
FIG. 10 depicts a $2^{nd}$ derivative spectrum of FIG. 9 polyamine as described below.

The polyketone in dry dichloromethane at −1° C. reacted smoothly with 2-propylamine to give the Schiff base (polyimines) in good to excellent yield shown in FIG. 7. The polyimine adduct was first characterized by FT-IR spectroscopy (FIG. 8), followed by $^{13}$C-NMR spectrum. The obtained $^{13}$C-NMR spectrum showed that the most downfield resonances observed were only those of the ester carbonyl absorbances at 173.19, 172.77, 172.46, and ppm (C=O ester) which correspond to the polar head group ester functionalities of the triglyceride. Reduction of the polyimines was carried out with sodium borohydride using the method of Haire (Haire, M. J., J. Org. Chem., 42(21): 3446 (1977)) although reduction with an amalgam or hydrogen may be cheaper. The polyamine isolated was a reddish viscous liquid. Its FT-IR spectrum (FIG. 9) showed a prominent characteristic N—H stretching mode of secondary amines at 3384 cm$^{-1}$ and C—N stretching bands at 1668 and 1551 cm$^{-1}$. In FIG. 10 is shown the $2^{nd}$ derivative spectrum of FIG. 9 and indicates the only carbonyl bands present being those of the glyceryl backbone ester carbonyl absorption at 1755 cm$^{-1}$. The N—H stretch was observed around 3500 cm$^{-1}$. The pH of this polyamine was slightly higher than 8 in non-aqueous media and therefore would function more effectively as chelating agent for metal ions as well as a neutralizing agent.

Example 2

Physical and viscosity properties of Milkweed Polyamine oil: The effect of temperature on the density and refractive index (RI) of milkweed polyamine as described in Example 1 is summarized in Table 1. The polyamine was denser than water. Table 2 compares the kinematic viscosities of milkweed oil and its polyamine derivatives as a function of temperature. Also compared in Table 2 are the viscosity indices (VIs) of the two oils. As shown in Table 2, surprisingly polyamination considerably increased the viscosity of milkweed oil at all temperatures. At 40° C., the viscosity surprisingly displayed an almost twenty-fold increase, and at 100° C. an almost six-fold increase. This means polyamination will increase the viscosity range for the application of milkweed oil in lubrication. Table 2 also shows that polyamination surprisingly resulted in considerable reduction of the VI of milkweed oil, almost to half of the parent oil. Even though the VI of milkweed polyamine is considerably below those of vegetable oils, it is still comparable with petroleum-based oils widely used in lubrication. Thus, milkweed polyamine can still be competitive with petroleum-based oils for application in lubrication.

Oxidation stability and cold flow properties of Milkweed Polyamine oil: Table 3 summarizes the cold flow and oxidation stability data for milkweed polyamine oil. Cold flow properties were evaluated using pour point (PP) and cloud point (CP) data. As shown in Table 3, only PP data could be generated for milkweed polyamine oil since the oil was dark red and clouding could not be easily detected during the test. In general, oils with PP values of double digit below zero are preferred for lubrication applications. However, a PP below freezing, such as that for milkweed polyamine oil, is surprisingly not considered bad since it can be easily improved with the use of low concentrations of pour point depressants.

Table 4 also shows the results of oxidation stability tests by the PDSC (Pressure Differential Scanning Calirimeter) method. In this method, the temperature at which oxidation of the oil under oxygen atmosphere begins (OT) and peaks (PT) are reported. The higher the values of OT and PT, the higher the oxidation stability of the oil. Table 3 compares the OT and PT of milkweed polyamine oil with those of milkweed oil. As seen in Table 3, polyamination surprisingly resulted in considerable improvement in the oxidative stability of milkweed oil. Both OT and PT have increased by almost 40° C. after polyamination. Without being bound by theory, there could be many reasons for this improvement in oxidative stability due to polyamination; a major contributor to such an improvement is the elimination of unsaturation in the oil structure, which eliminates reactive allylic and bisallylic protons, which are considered major contributors to oil oxidation.

Example 3

Tribological properties: The polyamine triglyceride of Example 1 was subjected to tribological tests conducted on a 4-ball tribometer. The 4-ball tests were conducted on a model KTR-30L 4-ball tribometer (Koehler Instruments, Bohemia, N.Y.). The instrument comprises a mechanical unit, electronic unit, and a computer with TriboDATA software (Koehler Instruments, Bohemia, N.Y.) that allows for setting and controlling test parameters as well as for automatic data acquisition. Test balls used in 4-ball experiments were obtained from Falex Corporation (Aurora, Ill.) and had the following specifications: material, chrome-steel alloy made from AISI E52100 standard steel; hardness, 64-66 $R_c$; diameter, 12.7 mm; finish, grade 25 extra polish. Test balls were degreased by two consecutive sonications in isopropyl alcohol and hexane solvents in an ultrasonic bath prior to use. The pot and spindle used for securing the balls were also thoroughly washed with isopropyl alcohol and hexane, wiped with Kimwipe® (Kimberly-Clark Worldwide, Inc., Roswell, Ga.), and allowed to air dry prior to testing with a new lubricant.

In this configuration, friction was measured between one rotating top steel ball pressed by the specified load against three stationary bottom steel balls in the test lubricant. At the end of the test, the wear scar diameters (WSD) on the three bottom balls was measured, averaged and reported. The two types of tests conducted on a 4-ball tribometer were Anti-Wear test (AW) and Extreme Pressure (EP) test. The AW test was conducted at 75° C. for 1 h using a relatively light load of 392 N. In the AW test, the frictional torque was measured continuously and, when the test stopped, the WSD on the balls was measured. The frictional torque was converted into coefficient of friction (COF) using standard procedures. The EP test has no load limits and involves a series of short time tests (10 s) with progressively increasing load, until the lubricant fails, which is indicated by welding of the four balls. The minimum load at which welding of the four balls occurs was determined to be the weld point (wp) of the lubricant and described in ASTM D2783-03(2014), Standard Test Method for Measurement of Extreme-Pressure Properties of Lubricating Fluids (Four-Ball Method).

Table 4 shows the results of AW and EP tests on milkweed polyamine oil of Example 1. The data in Table 4 indicates that milkweed polyamine oil surprisingly displayed the lowest average COF and the second lowest WSD among the four derivatives. Milkweed polyamine oil showed an EP WP of 140 kgf, which indicated that the oil lacks any significant EP properties. This was not surprising since none of the elements comprising milkweed polyamine oil (C, H, O, N) are expected to display EP characteristics.

Effect of chemical structure: Table 5 compares available properties of milkweed oil and several of its derivatives, viz., polyepoxy; polyamine; acetate, butyrate, and valerate polyesters; and polyhydroxy. Table 5 compares the kinematic viscosity, VI, cold flow (PP, CP), and oxidation stability (OS) determined using PDSC (OT and PT) of MWO and the listed derivatives. In Table 5, the oils were arranged in order of increasing kinematic viscosity from left to right. As can be seen in Table 5, the kinematic viscosity of MWO surprisingly increased dramatically due to derivatization. Kinematic viscosity increased in the order: MWO<polyepoxy<polyvalerate<polyamine<polybutyrate< polyacetate<polyhydroxy. Without being bound by theory, this trend can be explained in terms of intermolecular hydrogen bonding, which is greatest for the polyhydroxy derivative. The order for the polyesters and polyepoxide could be due to intermolecular polar interactions which is expected to increase in the order: polyoxirane<polyvalerate<polybutyrate<polyacetate. Based on structural considerations, the polyamine should have shown a much significantly higher intermolecular interaction and, therefore, significantly higher viscosity than all the polyesters. But the data surprisingly showed it positioned in the middle of the pack, as it were, the nitrogen with its tethered isopropyl group appears to impose a bulkiness and sphericity to the structure with a tendency to inhibit significant hydrogen bonding in the polyamine. Polar interactions though were slightly better than in the polyepoxide. The fact that the viscosity of the polyamine was lower than the polybutyrate and polyacetate implies the significant role branching on the nitrogen surprisingly plays in attenuating the observed polyamine viscosity.

Comparison of the VI of MWO and its derivatives in Table 5 shows an interesting correlation between the oil polarity and VI. Surprisingly MWO, which was the least polar of the oils, had the highest VI, whereas the polyhydroxy derivative, which was the most polar, had the lowest VI; the VI of the rest of the derivatives followed a similar trend and increased in the order: polyacetate<polyamine<polybutyrate<polyvalerate<polyepoxy. This observation was similar to what is widely known about the effect of polar hydroxyl groups on the VI of vegetable oils, such as castor oil, which has a VI of ~89, much lower than that for the non-polar vegetable oils such as milkweed, soybean, etc., whose VI is >200. Examination of Table 5 also shows the VI was a better predictor of polarity than kinematic viscosity, since it predicted the polarity of polyamine to be closer to polyacetate than to polyvalerate. Table 5 also shows the derivatization of MWO to the polyamine and polyacetate were not an effective method for improving the PP of MWO, whereas conversion to polybutyrate or polyvalerate was surprisingly more effective.

In Table 6 below are the sequestration data for silver and mercury ions which were determined in aqueous media using Soy polyketone oil, Soy-α-hydroxydibutylamine, Milkweed polyisopropyl amine (MW Pamine), and Osage orange α-hydroxydibutylamine derivatives. Derivation of the polyketone oils was via oxidation of the polyhydroxylated Milkweed and Soy to the polyketones. Milkweed polyketone was aminated with isopropylamine to give the Schiff Base followed by reduction to the MW Pamine as described above. The α-hydroxy dibutylamine derivatives of the oils were produced via aminolysis of the epoxidized starting oils with the appropriate amine moiety. Table 6 shows the chelation capacities of Soy polyketones for $Ag^+$ and $Hg^{2+}$ were surprisingly comparatively as good as or even better than the amine moieties; the advantage for the polyketone synthesis is achieved in fewer reaction steps than the amine. Below is a brief description of the enabling procedure for the ICP measurements of the sequestration capacities of the oil derivatives already evaluated for silver and mercury ions.

Inductively Coupled Plasma (ICP) measurements: Samples masses were accurately weighed as shown below in Table 6. To each sample, 1000 μL of stock silver solution and 1000 μL of stock mercury solution were added. The initial sample was a stock control sample. Each sample (including the control) was vortexed for approximately one minute and allowed to sit for two days before testing on the ICP. 1000 μL of the aqueous sample was extracted from the vial and diluted to volume in 10 mL volumetric flasks. The sample was then transferred to a labeled 15 mL centrifuge tube for testing on the ICP. A three point calibration curve was established with the use of a reagent blank. An independent verification sample was tested at the beginning and end of testing as well as periodically after every fifth sample. Unknown samples were tested at 328.068 nm for silver and at 253.652 nm for mercury. As observed in Table 6, surprisingly all the functionalized oil polyketones and polyamines removed mercury and silver from solution, albeit, some more predominantly than others.

Conclusions: The two Soy polyketone triglyceride oil trials surprisingly removed 95.2% and 96.4% of the mercury from an aqueous stock solution, respectively. Surprisingly, the Soy polyketone also removed 43.4% and 45.4%, respectively of the contained silver from the same aqueous stock solution.

Analogously, the Milkweed polyamine triglycerides (MW Pamine) trials surprisingly removed 91.9%, 56.4%, 82.6%, and 47.2% of the mercury from an aqueous stock solution, respectively. Surprisingly, the Milkweed polyamine triglycerides (MW Pamine) trials also removed 37%, 14.5%, 24.2%, and 16.7% of the silver respectively from the same aqueous stock solutions.

The Soy dibutylamine (Soydba) and Osage orange dibutylamine contains only about half the amine content of the Milkweed polyamine triglycerides (both of these were derived from aminolysis of the oxiranes thus yielding α-hydroxydibutylamines). The Soy dibutylamine (Soydba) removed 68.2% of the mercury and 58.8% of the silver from the same aqueous stock solution. The Osage orange dibutylamine oil α-hydroxy groups were acetylated yielding an oil which removed 89.5% of the mercury and 42.5% of the silver.

All of the references cited herein, including U.S. Patents and U.S. Patent Application Publications, are incorporated by reference in their entirety.

Thus, in view of the above, there is described (in part) the following:

A polyketone triglyceride composition containing 8 to 16 ketone carbonyl moieties per triglyceride unit.

The above polyketone triglyceride composition, where said composition is made by a method comprising (or consisting essentially of or consisting of) providing a hydroxyl vegetable oil triglyceride having 8 to 16 hydroxyl moieties per triglyceride unit, reacting said hydroxyl moieties with an oxidant, and isolating a polyketone triglyceride from the reaction of said hydroxyl vegetable oil triglyceride having 8 to 16 hydroxyl moieties per triglyceride unit and said oxidant; wherein said method utilizes a non-aqueous solvent.

A method for making a polyketone triglyceride composition, said method comprising (or consisting essentially of or consisting of) providing a hydroxyl vegetable oil triglyceride having 8 to 16 hydroxyl moieties per triglyceride unit, reacting said hydroxyl moieties with an oxidant, and isolating a polyketone triglyceride from the reaction of said hydroxyl vegetable oil triglyceride having 8 to 16 hydroxyl moieties per triglyceride unit and oxidant; wherein said method utilizes a non-aqueous solvent.

A method to remove metal species from a material suspected of containing one or more metal ion species, said method comprising (or consisting essentially of or consisting of) contacting said material with a polyketone triglyceride for a period of time and under conditions effective for sequestering said metal species by said polyketone triglyceride, and separating said polyketone triglyceride from said material.

A lubricant formulation comprising (or consisting essentially of or consisting of) the above polyketone triglyceride composition. The lubricant formulation, further comprising a base oil, friction modifier additive or both as an oil and additive.

A polyimine triglyceride composition having has 8 to 16 nitrogen moieties per triglyceride unit.

The above polyimine triglyceride composition, said composition made by a method comprising (or consisting essentially of or consisting of) providing a polyketone vegetable oil triglyceride having 8 to 16 ketone moieties per triglyceride unit, and reacting said ketone moieties with a primary amine moiety to form a polyimine adduct.

A method for making a polyimine triglyceride, said method comprising (or consisting essentially of or consisting of) providing a polyketone vegetable oil triglyceride having 8 to 16 ketone moieties per triglyceride unit, and reacting said ketone moieties with a primary amine moiety to form a polyimine adduct; wherein said method utilizes a non-aqueous solvent.

A method to remove metal species from a material suspected of containing one or more metal ion species, said method comprising (or consisting essentially of or consisting of) contacting said material with a polyimine triglyceride thereof for a period of time and under conditions effective for sequestering said metal species by said polyamine triglyceride thereof, and separating said polyimine triglyceride from said material.

A lubricant formulation comprising the above polyimine triglyceride composition. The lubricant formulation, further comprising a base oil, friction modifier additive or both as an oil and additive.

A polyamine triglyceride composition containing 8 to 16 nitrogen moieties per triglyceride unit.

The above polyamine triglyceride composition, where said composition is made by a method comprising (or consisting essentially of or consisting of) providing a polyketone vegetable oil triglyceride having 8 to 16 ketone moieties per triglyceride unit, reacting said ketone moieties with a primary amine moiety to form a polyimine adduct, and reducing said polyimine adduct to form said polyamine triglyceride.

A method for making a polyamine triglyceride composition, said method comprising (or consisting essentially of or consisting of) providing a polyketone vegetable oil triglyceride having 8 to 16 ketone moieties per triglyceride unit, reacting said ketone moieties with a primary amine moiety to form a polyimine adduct, and reducing said polyimine adduct to form said polyamine triglyceride.

A method to remove metal species from a material suspected of containing one or more metal ion species, said method comprising (or consisting essentially of or consisting of) contacting said material with a polyamine triglyceride thereof for a period of time and under conditions effective for sequestering said metal species by said polyamine triglyceride thereof, and separating said polyamine triglyceride from said material.

A lubricant formulation comprising the above polyamine triglyceride composition. The lubricant formulation, further comprising a base oil, friction modifier additive or both as an oil and additive.

The term "consisting essentially of" excludes additional method (or process) steps or composition components that substantially interfere with the intended activity of the method (or process) or composition.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Density and refractive index of Milkweed Polyamine oil

| T, °C. | RI | density, g/cm$^3$ |
|---|---|---|
| 25 | | 1.0209 ± 0.0001 |
| 30 | 1.4694 ± 0.0002 | 1.0171 ± 0.0001 |
| 40 | 1.4651 ± 9.6E−05 | 1.0093 ± 0.0002 |
| 75 | 1.4530 ± 0.0003 | 0.9820 ± 0.0003 |
| 100 | 1.4439 ± 0.0017[b] | 0.9642 ± 0.0007 |

[b]RI data at 100° C. is extrapolated from measured data at ≤80° C.

TABLE 2

Kinematic viscosity and viscosity index (VI) of milkweed oil (MWO) and its polyamine derivative

| kVis mm$^2$/s | MWO | MW polyamine |
|---|---|---|
| 40° C. | 33.8 | 581.01 ± 16.69 |
| 75° C. | | 95.80 ± 0.05 |
| 100° C. | 7.3 | 41.60 ± 0.60 |
| VI | 210 | 116 |

TABLE 3

Cold flow (pour point, cloud point) and oxidation stability (by PDSC) properties of milkweed oil and milkweed polyamine

| | Milkweed Oil | Milkweed Polyamine Oil |
|---|---|---|
| Cold Flow | | |
| Pour Point, ° C. | | −4.3 ± 0.6 |
| Cloud Point, ° C. | | |
| Oxidation Stability | | |
| PDSC - OT, ° C. | 136.78 ± 0.35 | 173.49 ± 0.79 |
| PDSC - PT, ° C. | 154.32 ± 0.47 | 194.18 ± 0.07 |

TABLE 4

Anti-wear (AW) and extreme pressure (EP) properties of milkweed oil derivatives

| | MW polyamine | MW polyesters | | |
| --- | --- | --- | --- | --- |
| | | valerate | Butyrate | acetate |
| Anti-Wear | | | | |
| COF | 0.050 ± 0.001 | 0.055 ± .005 | 0.064 ± 0.014 | 0.059 ± 0.008 |
| wsd, mm | 0.593 ± 0.011 | 0.778 ± 0.058 | 0.622 ± 0.067 | 0.576 ± 0.030 |
| EP | | | | |
| weld point, kgf | 140 | | | |

TABLE 5

Selected properties of milkweed oil (MWO) and certain derivatives

| | MWO | polyepoxy | polyamine | Polyesters | | | polyhydoxy |
| --- | --- | --- | --- | --- | --- | --- | --- |
| | | | | valerate | butyrate | Acetate | |
| kVis, mm²/s | | | | | | | |
| 40° C. | 33.8 (b) | 164.4 (b) | 581.01 ± 16.69 | 489.4 (b) | 926.2 (b) | 1733 (b) | 2332 (b) |
| 75° C. | | | 95.80 ± 0.05 | | | | |
| 100° C. | 7.3 (b) | 19.22 (b) | 41.60 ± 0.60 | 42.2 (b) | 63.2 (b) | 78 (b) | 75.5 (b) |
| VI | 210 (b) | 133 (b) | 116 | 136 (b) | 131 (b) | 105 (b) | 85 (b) |
| Cold Flow | | | | | | | |
| PP, ° C. | | −4.3 ± 0.6 | −18 (b) | −18 (b) | −3 (b) | −15 (b) | |
| CP, ° C. | | | −28 (b) | −30 (b) | −25 (b) | −7 (b) | |
| OS by PDSC | | | | | | | |
| OT, ° C. | 136.78 ± 0.35 | | 173.49 ± 0.79 | | | | |
| PT, ° C. | 154.32 ± 0.47 | | 194.18 ± 0.07 | | | | |
TABLE 6

ICP data of heavy metal sequestration by polyketo- and polyamine oils

| Oil Descriptor | Oil mass (g) | Analysis | [Ag] (ppm) | [Hg] (ppm) | [Ag] (%) | [Hg] (%) |
| --- | --- | --- | --- | --- | --- | --- |
| stock solution | | ICP | 302.5 | 297.3 | 0.0 | 0.0 |
| Soy polyketones (Spk2) | 0.1003 | ICP | 171.3 | 10.73 | −43.4 | −96.4 |
| Soy polyketones (unrefrigerated) | 0.1048 | ICP | 165.3 | 14.37 | −45.4 | −95.2 |
| MW Pamine (unrefrigerated) | 0.1217 | ICP | 190.6 | 24.15 | −37.0 | −91.9 |
| MW Pamine (refrigerated) | 0.1683 | ICP | 258.6 | 129.5 | −14.5 | −56.4 |
| MW Pamine (unrefrigerated) | 0.1090 | ICP | 229.4 | 51.64 | −24.2 | −82.6 |
| MW Pamine (refrigerated) | 0.1200 | ICP | 252.1 | 156.9 | −16.7 | −47.2 |
| Soy dibutylamine (refrigerated) | 0.1150 | ICP | 256.6 | 154.8 | −15.2 | −47.9 |
| Soydba | 0.1190 | ICP | 124.6 | 94.62 | −58.8 | −68.2 |
| Osage orange dibutylamine acetate (2) | 0.1012 | ICP | 173.8 | 31.22 | −42.5 | −89.5 |
| Osage orange dibutylamine acetate | 0.1189 | ICP | 235.8 | 49.68 | −22.0 | −83.3 |

We claim:

1. A polyketone triglyceride composition containing 8 to 16 ketone carbonyl moieties per triglyceride unit.

2. The polyketone triglyceride composition of claim 1, wherein said composition is made by a method comprising providing a hydroxyl vegetable oil triglyceride having 8 to 16 hydroxyl moieties per triglyceride unit, reacting said hydroxyl moieties with an oxidant, and isolating a polyketone triglyceride from the reaction of said hydroxyl vegetable oil triglyceride having 8 to 16 hydroxyl moieties per triglyceride unit and said oxidant; wherein said method utilizes a non-aqueous solvent.

3. A method for making a polyketone triglyceride composition, said method comprising providing a hydroxyl vegetable oil triglyceride having 8 to 16 hydroxyl moieties per triglyceride unit, reacting said hydroxyl moieties with an oxidant, and isolating a polyketone triglyceride from the reaction of said hydroxyl vegetable oil triglyceride having 8 to 16 hydroxyl moieties per triglyceride unit and oxidant; wherein said method utilizes a non-aqueous solvent.

4. A lubricant formulation comprising the polyketone triglyceride composition of claim 1.

5. The lubricant formulation of claim 4, further comprising a base oil, friction modifier additive or both as an oil and additive.

6. A method to remove metal species from a material suspected of containing one or more metal ion species, said method comprising contacting said material with a polyketone triglyceride containing 8 to 16 ketone carbonyl moieties per triglyceride unit for a period of time and under conditions effective for sequestering said metal species by said polyketone triglyceride, and separating said polyketone triglyceride from said material.

* * * * *